United States Patent

Shieh et al.

[11] Patent Number: 6,057,167
[45] Date of Patent: May 2, 2000

[54] MAGNETORESISTANCE-BASED METHOD AND APPARATUS FOR MOLECULAR DETECTION

[75] Inventors: Chan-Long Shieh, Paradise Valley, Ariz.; Donald E. Ackley, Lambertville, N.J.

[73] Assignee: Motorola, Inc., Schaumburg, Ill.

[21] Appl. No.: 08/656,647

[22] Filed: May 31, 1996

[51] Int. Cl.[7] .................................................. G01N 33/553
[52] U.S. Cl. ..................... 436/526; 324/252; 360/113; 422/82.02; 436/149; 436/151; 436/806
[58] Field of Search ............................ 324/252; 360/113; 422/82.02; 436/526, 149, 151, 806

[56] References Cited

U.S. PATENT DOCUMENTS

| | | |
|---|---|---|
| 4,219,335 | 8/1980 | Ebersole . |
| 4,835,509 | 5/1989 | Yoshino et al. ........................ 338/32 R |
| 5,006,906 | 4/1991 | Deri .......................................... 357/16 |
| 5,074,977 | 12/1991 | Cheung et al. ....................... 204/153.1 |
| 5,466,348 | 11/1995 | Holm-Kennedy . |
| 5,502,325 | 3/1996 | Sokolich et al. ........................ 257/421 |

FOREIGN PATENT DOCUMENTS

| | | |
|---|---|---|
| 0139373 | 5/1985 | European Pat. Off. . |
| 63-108264 | 5/1988 | Japan . |
| 97/45740 | 4/1997 | WIPO . |

*Primary Examiner*—Christopher L. Chin
*Attorney, Agent, or Firm*—James E. Gauger

[57] ABSTRACT

A binding of a molecule with a molecular receptor at a binding site is sensed using a magnetoresistive member proximate to the binding site. A magnetic field associated with the molecule acts to modify an electrical characteristic of the magnetoresistive member when the molecule binds with the molecular receptor. The magnetic field is produced by a magnetic member, such as a magnetic bead, attached to the molecule. Preferably, the magnetoresistive member is integrated with a substrate which supports the binding site. A readout device, such as a thin-film transistor, can also be integrated on the substrate to provide a signal indicative of a binding event.

14 Claims, 5 Drawing Sheets

MAGNETORESISTANCE-BASED METHOD AND APPARATUS FOR MOLECULAR DETECTION

FIELD OF THE INVENTION

The present invention relates to methods and systems for molecular detection.

BACKGROUND OF THE INVENTION

An increased effort has been directed toward the development of chips for molecular detection. In general, a molecular detection chip includes a substrate on which an array of binding sites is arranged. Each binding site, or hybridization site, has a respective molecular receptor which binds or hybridizes with a molecule having a predetermined structure.

A sample solution is applied to the molecular detection chip, and molecules in the sample bind or hybridize at one or more of the binding sites. The particular binding sites at which hybridization occurs are detected, and one or more molecular structures within the sample are subsequently deduced.

Of great interest are molecular detection chips for gene sequencing. These chips, often referred to as DNA chips, utilize an array of selective binding sites each having respective single-stranded DNA probes. A sample of single-stranded DNA fragments, referred to as target DNA, is applied to the DNA chip. The DNA fragments attach to one or more of the DNA probes by a hybridization process. By detecting which DNA probes have a DNA fragment hybridized thereto, a sequence of nucleotide bases within the DNA fragment can be determined.

To hasten the hybridization process, a local concentration of target DNA can be increased at predetermined sites using electric field enhancements. Here, each site has an electrode associated therewith for selectively generating an electric field thereby. The electric field is generated by applying an electric potential between an electrode at the site and a counter electrode at a peripheral portion of the chip. To attract DNA fragments to the site, the polarity of the electric potential is selected to generate an electric field having a polarity opposite to the charge of the DNA fragments. To dehybridize the site, an electric field having the same polarity as the DNA fragments can be generated to repel the DNA fragments from the site.

Various approaches have been utilized to detect a hybridization event at a binding site. In some systems, a fluorescence or a scattering of light associated with the hybridization event is optically sensed to detect the hybridization event. A difficulty with this approach is in the differentiation of the fluorescence or scattering associated with the hybridization from background fluorescent or scatter light. To achieve a sufficient signal-to-noise quantity, expensive optical detectors such as confocal microscopes or cooled CCD cameras are utilized.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

DETAILED DESCRIPTION OF A PREFERRED EMBODIMENT

Embodiments of the present invention advantageously provide a method and apparatus for sensing target molecules, such as antibodies, DNA strands, or other biopolymers, having an enhanced magnetic property. In particular, the structure of each of the target molecules is modified to include a magnetic member. A magnetoresistive member is located at a binding site to sense a magnetic field from target molecules proximate thereto. Hence, the magnetoresistive member can sense target molecules bound to molecular receptors at the binding site. This approach is advantageous in terms of sensitivity and background noise suppression since no naturally magnetic background molecules are encountered, and since the magnetoresistance effect is effectively confined to a surface of the magnetoresistive member.

Figure 1:
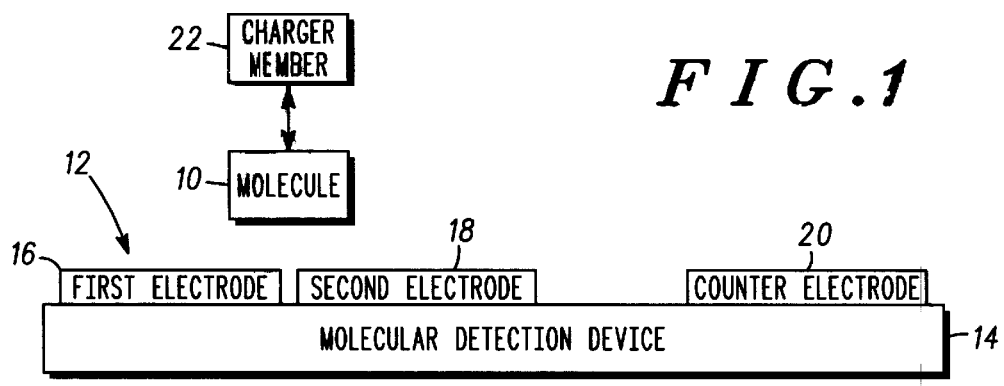
FIG. 1 is a block diagram of an embodiment of an apparatus for sensing a binding of a molecule to a molecular receptor.

FIG. 1 is a block diagram of an embodiment of an apparatus for sensing a binding of a molecule 10 to a molecular receptor 12. In general, the molecular receptor 12 is selected in dependence upon the molecule 10 which is to be detected. The molecular receptor 12 typically includes a biological or synthetic molecule having a specific affinity to the molecule 10 to be detected.

The molecular receptor 12 can include a chain of at least one nucleotide which hybridizes with a complementary chain of at least one nucleotide included in the molecule 10. Here, for example, the molecular receptor 12 can include a DNA probe for detecting a corresponding, complementary DNA sequence in the molecule 10. It is noted, however, that the scope of the present invention is not limited to sensing the hybridization of DNA molecules. Embodiments of the present invention can be utilized in applications which include, but are not limited to, detection of antibody-antigen binding events (wherein the molecule 10 and the molecular receptor 12 include an antibody-antigen pair) and detection of other biopolymer target molecules.

The apparatus includes a substrate 14 which supports a binding site 16 for receiving the molecular receptor 12. The apparatus further includes a magnetoresistive member 18 integrated with the substrate 14 and located proximate to the binding site 16. In general, the magnetoresistive member 18 is formed of a material having a conductance or a resistance which is dependent upon its magnetization. The conductance or the resistance can be dependent upon the magnitude of the magnetization, and a direction of magnetization relative to the direction of current flow in the magnetoresistive member 18. Hence, the magnetoresistive member 18 has a conductance, or equivalently a resistance, which is modified by a magnetic field associated with the molecule 10 when the molecule 10 comes in proximity thereto. This proximity can occur, for example, when the molecule 10 binds to the molecular receptor 12.

At least a portion of the magnetic field associated with the molecule 10 is from a magnetic member 20 attached to the molecule 10. The magnetic member 20 is utilized to significantly enhance the magnitude of the magnetic field associated with the molecule. Preferably, substantially all of magnetic field associated with the molecule 10 is generated by the magnetic member 20.

The magnetic member 20 has the form of a magnetic bead attached to the molecule 10. The magnetic bead can have a spherical form, with a diameter on the order of 0.1 to 1.0 $\mu$m. If the molecule 10 includes a polymer chain, the magnetic member 20 can be attached to an end of the polymer chain using conventional primer techniques. This allows the magnetic member 20 to be attached to an end of a DNA molecule, for example.

In general, the magnetoresistive member 18 can have any of a variety of shapes and/or forms using a variety of magnetoresistive materials. In one embodiment, the magnetoresistive member 18 has the form of a thin-film layer integrated with the substrate 14. The thin-film layer is formed of a magnetic material which exhibits the giant magnetoresistance effect. Here, the resistance of the thin-film layer is substantially enhanced, or equivalently, the conductance of the thin-film layer is substantially reduced, when the thin-film layer is subjected to a magnetic field. Other materials which exhibit a reduced resistance, rather than an enhanced resistance, when subjected to a magnetic field may also be utilized.

To read out a modified conductance or a modified resistance, the apparatus can further include a readout device 22 coupled to the magnetoresistive member 18. The readout device 22 produces a signal indicative of the modified conductance or the modified resistance of the magnetoresistive member 18 resulting from the magnetic field associated with the molecule 10. In a preferred embodiment, the readout device 22 includes a transistor, such as a thin-film transistor, integrated with the substrate 14.

Although illustrated in terms of a single molecular receptor at the binding site 16, it is noted that embodiments of the present invention are typically utilized with a plurality of like molecular receptors located at the binding site 16. Here, the plurality of like molecular receptors are utilized for detecting a predetermined molecular structure in a sample of target molecules. Further, it is noted that embodiments of the present invention typically have an array of binding sites supported by the substrate 14, rather than a single binding site as illustrated. Here, each of the binding sites can be utilized for detecting a different molecular structure within a sample of target molecules.

Figure 2:
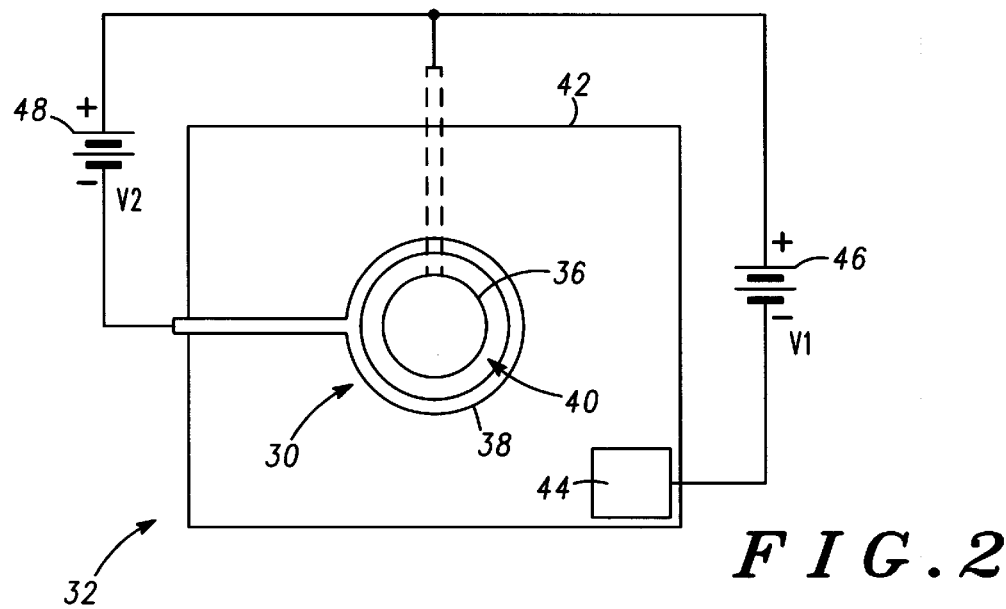
FIG. 2 is a block diagram of a preferred embodiment of an apparatus for sensing a binding of one or more molecules to one or more molecular receptors.

FIG. 2 is a block diagram of a preferred embodiment of an apparatus for sensing a binding of one or more molecules to one or more molecular receptors 30. The apparatus includes a substrate 32 which defines a binding site 34. A magnetoresistive layer 36 is integrated with the substrate 32. The magnetoresistive layer 36 is located in proximity to the binding site 34. Preferably, the magnetoresistive layer 36 includes a thin-film layer of a magnetic material capable of producing the giant magnetoresistance effect. The thin-film layer is deposited onto the substrate 32 using fabrication techniques known in the art.

Figure 7:
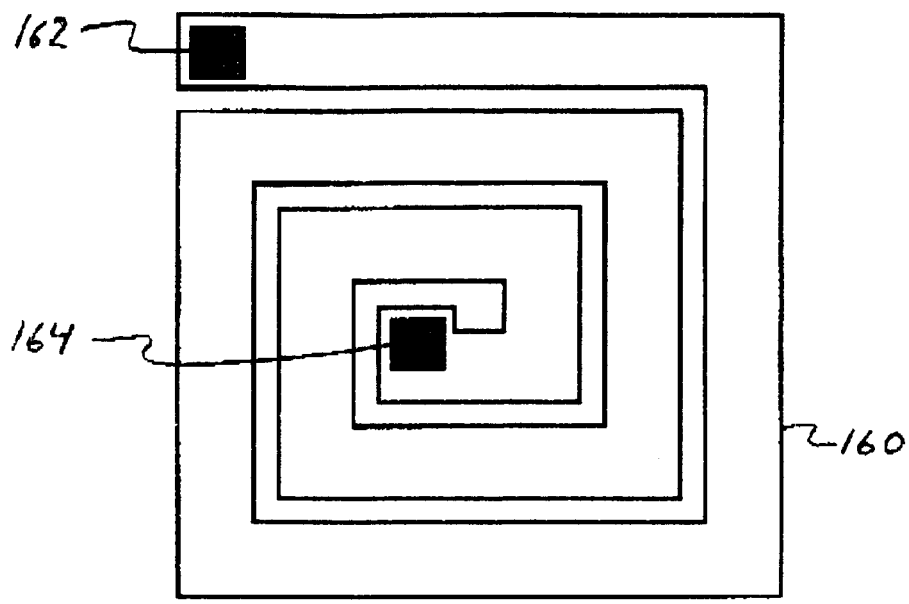
FIG. 7 is a top view of an alternative pattern of a magnetoresistive layer.
Figure 8:
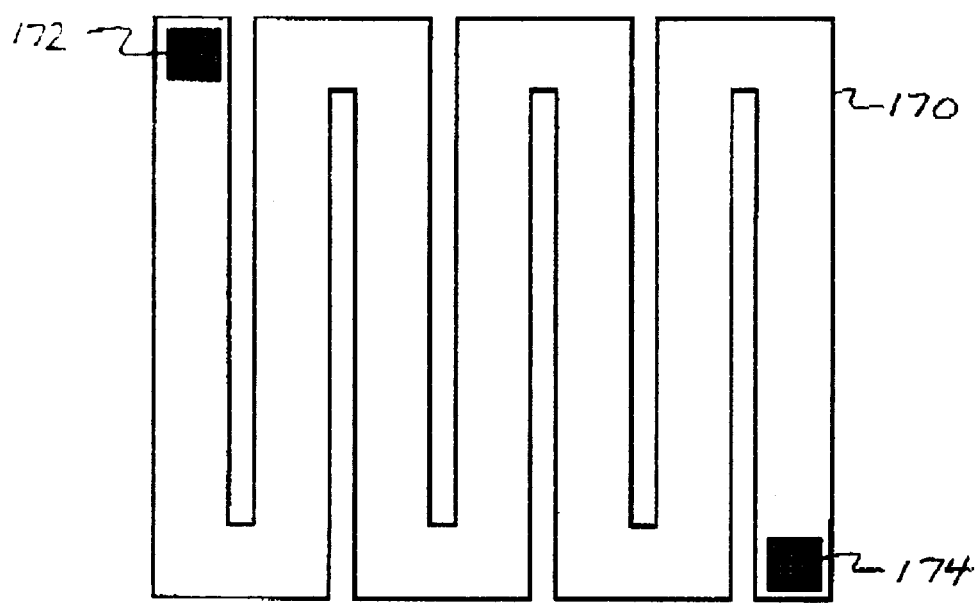
FIG. 8 is a top view of a second alternative pattern of a magnetoresistive layer.

Optionally, a plurality of interdigitated contacts is integrated with the substrate 32 to couple the magnetoresistive layer 36 to a readout device 40. The interdigitated contacts can be utilized to reduce the resistance sensed through the magnetoresistive layer 36. The use of the interdigitated contacts may be undesirable if the change in resistance of the magnetoresistive layer 36 is small when subjected to a magnetic field. Here, single contacts can be utilized to couple the magnetoresistive layer 36 to the readout device 40. Embodiments utilizing single contacts are illustrated in FIGS. 7 and 8.

In this embodiment, the readout device 40 has the form of a thin-film transistor which is integrated with the substrate 32. The thin-film transistor includes a source 42, a gate 44, and a drain 46. Either the source 42 or the drain 46 is coupled to a first set 48 of the interdigitated contacts by an interconnect 50 integrated with the substrate 32. The gate 44 is coupled to a second set 52 of the interdigitated contacts by an interconnect 54 integrated with the substrate 32. The plurality of interdigitated contacts and the readout device 40 are fabricated into the substrate using techniques known in the art.

The readout device 40 is utilized to read a change in resistance or conductance of the magnetoresistive layer 36. A change in the resistance of the magnetoresistive layer 36 is sensed by an output signal, formed at either the source 42 or the drain 46, in response to an input signal applied to the gate 44. The change in resistance is detected when the output signal is beyond a predetermined threshold. The input signal and the output signal can be in the form of either a voltage or a current, and can be either an AC signal or a DC signal.

Figure 3:
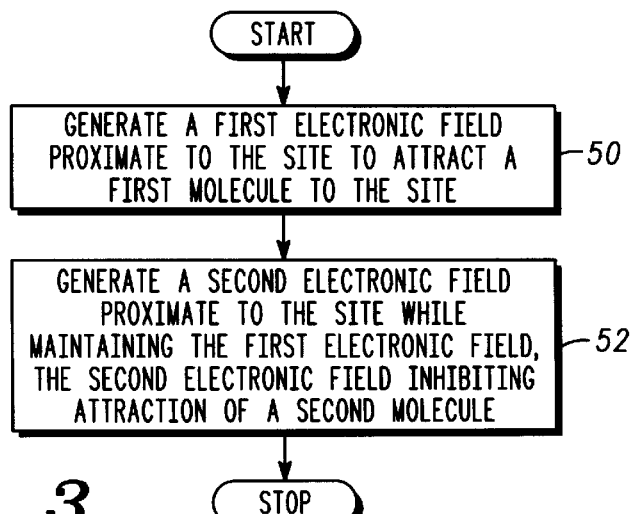
FIG. 3 is a flow chart of an embodiment of a method of sensing a binding of a molecule with a molecular receptor at a binding site in a molecular detection apparatus.

FIG. 3 is a flow chart of an embodiment of a method of sensing a binding of a molecule with a molecular receptor at a binding site in a molecular detection apparatus. As indicated by block 60, the method includes a step of providing a magnetoresistive member proximate to the binding site. It is preferred that the magnetoresistive member be provided in the context of any of the embodiments of a molecular detection apparatus as described herein. It is noted, however, that alternative embodiments of the method are not limited to these apparatus.

As indicated by block 62, the method includes a step of sensing a modified electrical characteristic of the magnetoresistive member when the molecule binds with the molecular receptor. The modified electrical characteristic results from a magnetic field associated with the molecule being proximate to the magnetoresistive member. As stated earlier, at least a portion of the magnetic field associated with the molecule, and preferably all of the magnetic field associated with the molecule, is from a magnetic member attached to the molecule.

Such an electrical characteristic which can be modified includes, but is not limited to, a DC resistance, a DC conductance, an AC resistance, an AC conductance of the magnetoresistive member. Hence, the step of sensing the modified electrical characteristic of the magnetoresistive member can include sensing a modified conductance or a modified resistance of the magnetoresistive member resulting from the magnetic field associated with the molecule. The modified conductance or modified resistance can be sensed either directly or indirectly, and can be sensed using either an AC signal or a DC signal applied to the magnetoresistive member.

As indicated by block 64, the method can further include a step of producing a signal indicative of the modified conductance or modified resistance of the magnetoresistive member resulting from the magnetic field associated with the molecule. The signal can be produced by a readout device coupled to the magnetoresistive member, such as the readout device 22 of FIG. 1. As illustrated in FIG. 2, the readout device can include a transistor which is integrated with a substrate which supports the binding site. Here, the readout device is coupled to the magnetoresistive member by a plurality of interdigitated contacts.

The signal produced by the readout device can be in the form of a voltage or a current, and can be either an AC signal or a DC signal. The signal is indicative of a modified conductance or a modified resistance when a measure thereof is beyond a predetermined threshold. The measure of the signal can be a DC level of either voltage or current. Alternatively, the measure of the signal can be a magnitude of an AC voltage or current.

Figure 4:
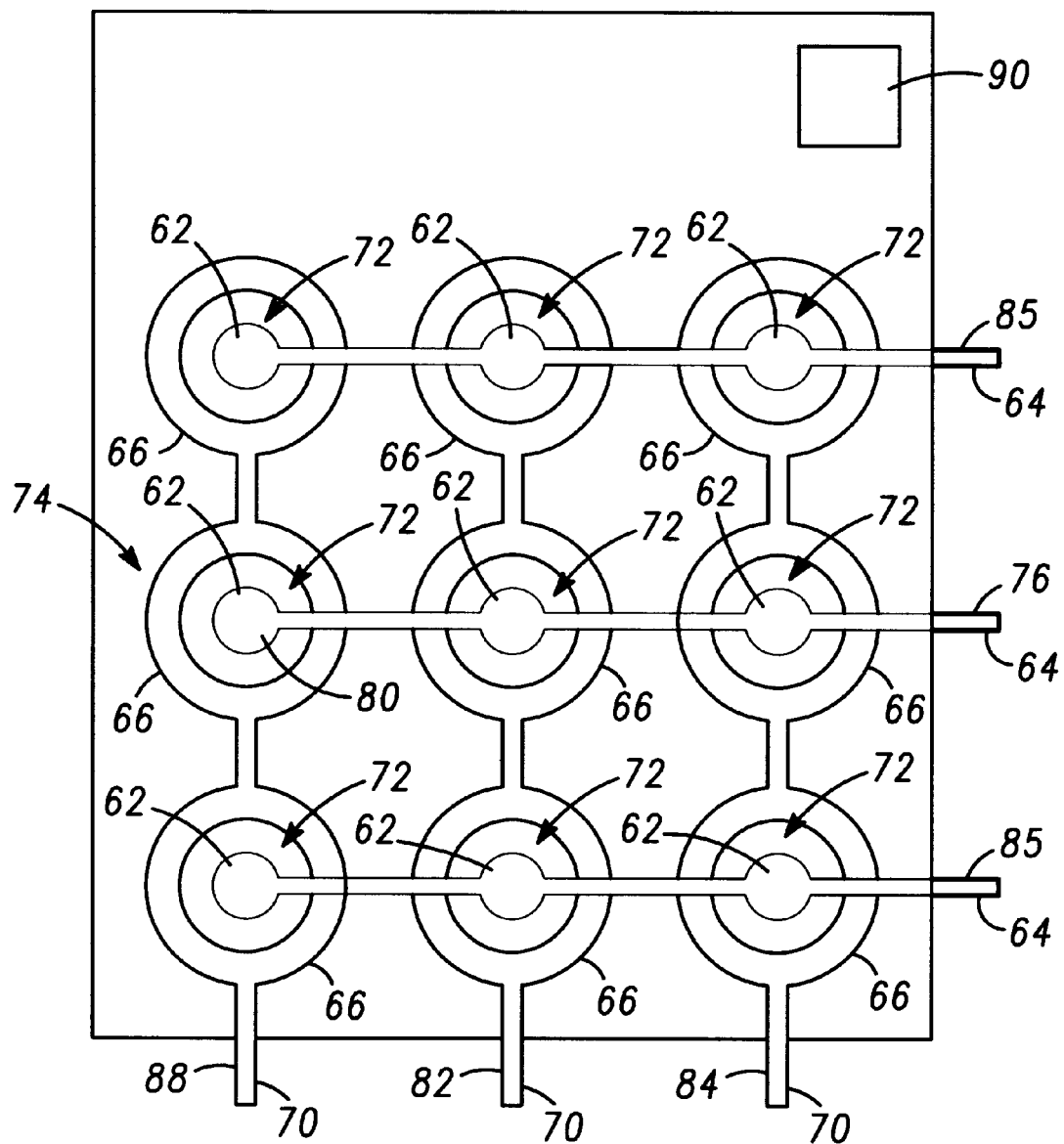
FIG. 4 illustrates the detection of a DNA hybridization event using an apparatus in accordance with the present invention.

FIG. 4 illustrates the detection of a DNA hybridization event using an apparatus in accordance with the present invention. The apparatus includes a first magnetoresistive layer 80 and a second magnetoresistive layer 82 supported by a substrate 84. The first magnetoresistive layer 80 is located proximate to a first binding site 86. The second magnetoresistive layer is located proximate to a second binding site 88.

The first binding site 86 receives a molecular receptor in the form of a first oligonucleotide probe 90. The first oligonucleotide probe 90 is attached to the first magnetoresistive layer 80 by a primer 92. Similarly, the second binding site 88 receives a molecular receptor in the form of a second oligonucleotide probe 96. The second oligonucleotide probe 96 is attached to the second magnetoresistive layer 82 by a primer 98.

For illustrative purposes, the first oligonucleotide probe 90 includes a T-T-G-C-C-A sequence of nucleotides, and the second oligonucleotide probe 96 includes an A-A-C-G-G-T sequence of nucleotides. As is known in the art, "A" is an abbreviation for adenine, "C" is an abbreviation for cytosine, "G" is an abbreviation for guanine, and "T" is an abbreviation for thymine. The first oligonucleotide probe 90 is utilized to detect molecules having a complementary sequence, namely an A-A-C-G-G-T sequence, of nucleotides therewithin. The second oligonucleotide probe 96 is utilized to detect molecules having a T-T-G-C-C-A sequence therewithin.

A sample of single-stranded DNA molecules is applied to the apparatus. Each of the single-stranded DNA molecules has a magnetic member 100 and 102 attached thereto. The first oligonucleotide probe 90 partially hybridizes with a G-A-C-G-G-T sequence of nucleotides within a first DNA molecule 104. The second oligonucleotide probe 96 fully hybridizes with a T-T-G-C-C-A sequence of nucleotides within a second DNA molecule 106. The binding energy of attachment is determined by the degree of match between the target molecules and the probes.

After hybridization, a wash or melt step can be performed to remove non-attached or poorly-attached target molecules. As a result, the first DNA molecule 104 would likely be removed from the first binding site 86, while the second DNA molecule 106 would likely remain at the second binding site 88. In general, the remaining attached target molecules are present in dependence upon the degree of matching to the probe molecules.

The magnetic member 102 attached to the second DNA molecule 106 modifies the resistance of the second magnetoresistive layer 82. The modified resistance is sensed to conclude that the sample of DNA molecules includes a T-T-G-C-C-A sequence within its structure.

Figure 5:
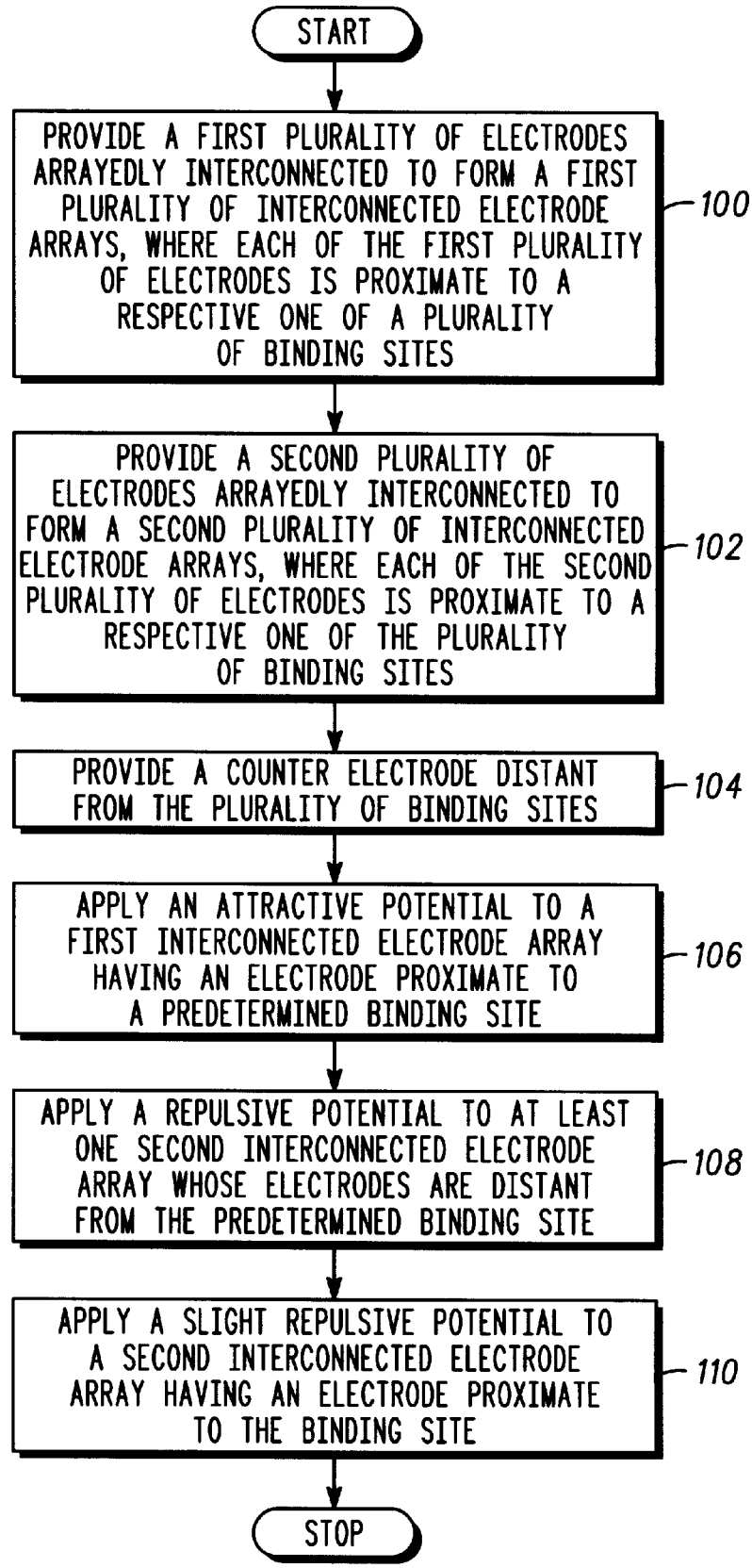
FIG. 5 is a schematic diagram of an embodiment of a circuit for detecting a binding of a molecule to a molecular receptor.

FIG. 5 is a schematic diagram of an embodiment of a circuit for detecting a binding of a molecule to a molecular receptor. The circuit is utilized to detect a change in the resistance of a magnetoresistive member, which is schematically represented by a resistor 120.

The resistor 120 is coupled between a gate 122 of a transistor 124 and ground 126. A source 128 of the transistor 124 is directly coupled to the ground 126. A reference resistor 130 is coupled between the gate 122 and a first voltage source, VBIAS. A load resistor 132 is coupled between a second voltage source, VDD, and a drain 134 of the transistor 124.

The reference resistor 130 and the magnetoresistive member (resistor 120) form a voltage divider which divides the first voltage source, VBIAS, for application to the gate 122. A change in the resistance of the magnetoresistive member (resistor 120) changes the voltage applied to the gate 122, and hence, changes the current which flows through the drain 134. The change in current through the drain 134 changes the voltage drop across the load resistor 132, and hence, changes the voltage at the drain 134. The voltage signal produced by the drain 134 is utilized to detect the binding event.

The transistor 124 can be embodied by the readout device 40 from FIG. 2. The reference resistor 130 and the load resistor 132 can be integrated with the substrate 32 which supports the magnetoresistive member and the readout device 40. Alternatively, the reference resistor 130 and the load resistor 132 can be externally-coupled components.

Figure 6:
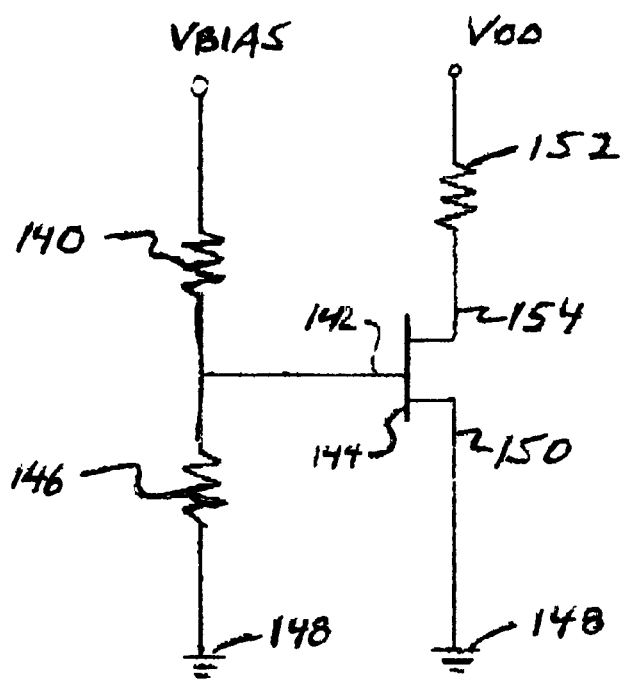
FIG. 6 is a schematic diagram of another embodiment of a circuit for detecting a binding of a molecule to a molecular receptor.

FIG. 6 is a schematic diagram of another embodiment of a circuit for detecting a binding of a molecule to a molecular receptor. The circuit is utilized to detect a change in the resistance of a magnetoresistive member, which is schematically represented by a resistor 140.

Here, the resistor 140 is coupled between a gate 142 of a transistor 144 and a first voltage source, VBIAS. A reference resistor 146 is coupled between the gate 142 and ground 148. The magnetoresistive member (resistor 140) and the reference resistor 146 form a voltage divider which divides the first voltage source, VBIAS, for application to the gate 142. A change in the resistance of the magnetoresistive member (resistor 140) changes the voltage applied to the gate 142.

As with the embodiment of FIG. 5, a source 150 of the transistor 144 is directly coupled to the ground 148, and a load resistor 152 is coupled between a second voltage source, VDD, and a drain 154 of the transistor 144. The change in resistance of the magnetoresistive member (resistor 140) changes the voltage at the drain 154. The voltage signal produced by the drain 154 is utilized to detect the binding event.

The transistor 144 can be embodied by a readout device integrated onto a substrate which supports the magnetoresistive member. The reference resistor 146 and the load resistor 152 can also be integrated with this substrate. Alternatively, the reference resistor 146 and the load resistor 152 can be externally-coupled components.

The magnetoresistive layer 36 in FIG. 2 is illustrated to have a substantially rectangular pattern. Alternative patterns for the magnetoresistive layer 36 are shown in FIGS. 7 and 8. These patterns are beneficial to increase the change in resistance of the magnetoresistive layer 36 when subjected to a magnetic field.

FIG. 7 is a top view of an alternative pattern of a magnetoresistive layer 160. Here, the magnetoresistive layer 160 is spiral-shaped (or serpentine-shaped) to increase the effective length between a first contact 162 and a second contact 164. Increasing the effective length acts to magnify changes in the resistivity of the magnetoresistive layer 160 as sensed by the resistance between the first contact 162 and the second contact 164.

FIG. 8 is a top view of a second alternative pattern of a magnetoresistive layer 170. The magnetoresistive layer 170 is zig-zag shaped to increase the effective length between a first contact 172 and a second contact 174. The increased length magnifies the changes in resistance sensed between the first contact 172 and the second contact 174.

Thus, there has been described herein a concept, as well as several embodiments including preferred embodiments of a magnetoresistance-based method and apparatus for molecular detection.

Because the various embodiments of the present invention magnetoresistively sense a magnetic field generated by a magnetic member attached to a nonmagnetic molecule, they provide a significant improvement in suppressing background noise from nonmagnetic background molecules. Further, since the giant magnetoresistance effect is effectively confined to the surface of the magnetoresistive member, the resulting sensitivity for detection is high.

Additionally, the various embodiments of the present invention as herein-described integrate the magnetoresistive member and a readout device with a substrate to form an integrated molecular detection device. In particular, an array of magnetoresistive member/readout device combinations can be formed on a substrate. The readout devices can be interconnected in a manner similar to active matrix display devices to provide for matrix addressing thereof.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. An apparatus for sensing a molecule having a magnetic member attached thereto, the magnetic member producing a magnetic field, the apparatus comprising:

a first magnetoresistive member;

a first molecular receptor including a first chain of a plurality of nucleotides complementary to a second chain of a plurality of nucleotides of the molecule, the first molecular receptor attached to the first magnetoresistive member so that when the molecule is hound with the first molecular receptor, the magnetic field from the magnetic member influences a magnetization-dependent characteristic of the first magnetoresistive member in accordance with a giant magnetoresistance effect; and a readout device coupled to the first magnetoresistive member to produce an electrical signal dependent upon the magnetization-dependent characteristic of the first magnetoresistive member when the molecule is bound with the molecular receptor.

2. The apparatus of claim 1 wherein the first molecular receptor includes at least one DNA probe, wherein the molecule includes a DNA molecule, and wherein the at least one DNA probe is complementary to the DNA molecule.

3. The apparatus of claim 1 further comprising a substrate, wherein the readout device includes a transistor integrated with the substrate, and wherein the transistor is coupled to the first magnetoresistive member.

4. The apparatus of claim 1 further comprising:

a second magnetoresistive member; and a second molecular receptor attached to the second magnetoresistive member, the second molecular receptor non-specific to the molecule.

5. The apparatus of claim 4 wherein the second molecular receptor includes a third chain of a plurality of nucleotides non-complementary to the second chain.

6. The apparatus of claim 4 further comprising a substrate having the first magnetoresistive member and the second magnetoresistive member integrated therewith.

7. A method of sensing a molecule having a magnetic member attached thereto, the method comprising the steps of:

providing the molecule having the magnetic member attached thereto, the magnetic member producing a magnetic field;

providing a magnetoresistive member;

providing a molecular receptor specifically bindable with the molecule, the molecular receptor attached to the magnetoresistive member so that when the molecule is bound with the molecular receptor, the magnetic field from the magnetic member influences a magnetization-dependent characteristic of the magnetoresistive member in accordance with a giant magnetoresistance effect; and sensing the magnetization-dependent characteristic of the magnetoresistive member when the molecule is bound with the molecular receptor.

8. The method of claim 7 wherein the magnetic member has a form of a bead.

9. The method of claim 7 wherein the molecular receptor includes a chain of a plurality of nucleotides, and wherein the molecule includes a complementary chain of a plurality of nucleotides.

10. The method of claim 9 wherein the molecular receptor includes at least one DNA probe, wherein the molecule includes a DNA molecule, and wherein the at least one DNA probe is complementary to the DNA molecule.

11. The method of claim 7 wherein the molecule and the molecular receptor include a complementary antibody-antigen specific binding pair.

12. The method of claim 7 wherein the step of sensing the magnetization-dependent characteristic of the magnetoresistive member includes sensing a magnetization-dependent conductance of the magnetoresistive member.

13. The method of claim 12 further comprising the steps of:

providing a readout device coupled to the magnetoresistive member; and producing an electrical signal indicative of the magnetization-dependent conductance of the magnetoresistive member using the readout device.

14. The method of claim 13 wherein the readout device includes a transistor coupled to the magnetoresistive member, wherein the transistor and the magnetoresistive member are integrated with a substrate.

* * * * *